United States Patent [19]

Reid et al.

[11] Patent Number: 5,043,274

[45] Date of Patent: Aug. 27, 1991

[54] PROCESS FOR PRODUCING AN OPTICALLY ACTIVE 2-ARYLPROPIONIC ACID

[75] Inventors: Alison J. Reid; Gareth T. Phillips, both of Sittingbourne, England; Arthur F. Marx, Delft, Netherlands

[73] Assignee: Shell Internationale Research Maatschappij B.V., The Haag, Netherlands

[21] Appl. No.: 340,830

[22] Filed: Apr. 20, 1989

[30] Foreign Application Priority Data

Apr. 21, 1988 [GB] United Kingdom ................ 8809434
Mar. 9, 1989 [GB] United Kingdom ................ 8905378

[51] Int. Cl.$^5$ .......................... C12P 7/62; C12P 7/40; C12P 41/00; C12R 1/00
[52] U.S. Cl. .................................... 435/135; 435/136; 435/141; 435/280; 435/822; 435/911

[58] Field of Search ............... 435/136, 141, 280, 822, 435/911, 135

[56] References Cited

U.S. PATENT DOCUMENTS 4,661,628 4/1987 Cannata et al. ..................... 562/401
4,886,750 12/1989 Bertola et al. ...................... 435/141

Primary Examiner—Herbert J. Lilling
Attorney, Agent, or Firm—Bierman and Muserlian

[57] ABSTRACT

A process for the preparation of S-2-(6-methoxy-2-naphthyl)propionic acid or a pharmaceutically acceptable salt or ester thereof, which comprises supplying R-2-(6-methoxy-2-naphthyl)-propionic acid or a pharmaceutically acceptable salt or ester thereof, to a microorganism having a stereospecific inverting enzyme system, or an extract of the microorganism containing said enzyme system, capable of converting the R enantiomer to the corresponding S enantiomer.

8 Claims, No Drawings

PROCESS FOR PRODUCING AN OPTICALLY ACTIVE 2-ARYLPROPIONIC ACID

This invention relates to the preparation of the optically active non-steroidal anti-inflammatory drug naproxen (S-2-(6-methoxy-2-naphthyl)propionic acid) and pharmaceutically acceptable salts and esters thereof.

Known processes for preparing naproxen involve the preparation and subsequent resolution of racemic 2-(6-methoxy-2-naphthyl)propionic acid, as described, for example, in European patent application publication number 143371. Since 50% of the racemic acid is the undesired R enantiomer, the maximum theoretical yield of such processes is 50%.

Surprisingly, it has now been found that the undesired R enantiomer can be converted into the desired S enantiomer by certain microorganisms.

According to this invention we provide a process for the preparation of S-2-(6-methoxy-2-naphthyl)propionic acid or a pharmaceutically acceptable salt or ester thereof, which comprises supplying R-2-(6-methoxy-2-naphthyl)propionic acid or a pharmaceutically acceptable salt or ester thereof, to a microorganism having a stereospecific inverting enzyme system, or an extract of the microorganism containing said enzyme system, capable of converting the R enantiomer to the corresponding S enantiomer.

Preferably the R-acid is supplied to the microorganism. It may be supplied to the microorganism substantially free of the S enantiomer, or in the form of a mixture with the S enanatiomer, for example a racemic mixture.

It will be appreciated that some microorganisms may be capable of hydrolysing esters of 2-(6-methoxy-2-naphthyl)propionic acid. Accordingly, when an ester of the R-acid is supplied to such microorganisms, the product of the process will be the S acid, not the S ester.

When the product is the free acid, this may, if desired, be converted to a pharmaceutically acceptable salt or ester by methods well known in the art.

The microorganism used in the process according to the invention may be a fungus or a bacterium.

Suitable fungi for carrying out the process include members of the genus Botrytis, Penecillium, or preferably, Cordyceps, Beauveria, Cladosporium, or Exophiala, for example the species *Cordyceps militaris, Beauveria bassiana, Cladosporium resinae, Exophiala jeanselmei* and *Exophiala wilhansii*. Suitable bacteria for carrying out the process include members of the genus Norcardia, Bacillus, Pseudomonas, Mycobacterium, Arthrobacter, Leuconostoc, Proteus or Streptomyes, or preferably, Rhodococcus, for example the species *Rhodococcus, rhodochrous.*

Examples of such species are: *Cordyceps militaris* CBS 267.85 and *Exophiala jeanselmei* CBS 258.86 deposited with the Centraalbureau voor Schimmelcultures (CBS), The Netherlands on 7 June 1985 (CBS 267.85) and 15 May 1986 (CBS 258.86); *Exophiala wilhansii* (CBS 547.88) deposited with the Centraalbureau voor Schimmelcultures (CBS), The Netherlands on 6th Sept., 1988; *Rhodococcus rhodochrous* NCIB 12566 deposited with the National Collections of Industrial and Marine Bacteria, U.K. on 16 Oct. 1987; *Beaveria bassiana* DSM 875, ATCC 13144, redeposited at the Commonwealth Mycological Institute, U.K. on 13th June 1988 under CMI 325429; *Cladosporium resinae* CBS 177.62 redeposited as *Hormoconis resinae* at the Commonwealth Mycological Institute, U.K. on 13th June, 1988 under number 325430; and variants or mutants thereof.

While the stereospecific inversion is usually carried out in the presence of the whole cells, the stereospecific inverting enzyme system may have been completely or partly extracted from the microorganism prior to carrying out the inversion. To avoid unnecessary separation, enzyme purification and enzyme immobilisation procedures, the enzyme is usually present with at least some of the cell components. When in association with the cells, these may be live or dead, intact, treated in some way or themselves immobilised and optionally homogenised, so long as the enzyme component itself is retained in active and stable form to allow the inversion to proceed. Immobilisation of the enzyme or the cells may be by any of the methods known in the art so long as the enzyme inverting activity is retained intact.

The microorganisms are preferably cultured prior to use for the stereospecific inversion for about 1 to 10 days, whereafter the cells are suspended in a liquid nutrient medium, preferably a minimal liquid nutrient medium, and 2-(6-methoxy-2-naphthyl)propionic acid is subjected to the action of the cells. After the abovementioned cultivation the cells may be isolated from the culturing medium before suspending the cells in the minimal liquid nutrient medium. To grow the microorganisms used for the stereospecific, ordinary culture media containing an assimilable carbon source (for example glucose, lactate, sucrose, etc.), a nitrogen source (for example ammonium sulphate, ammonium nitrate, ammonium chloride, etc.), with an agent for an organic nutrient source (for example yeast extract, malt extract peptone, meat extract, etc.) and an inorganic nutrient source (for example phosphate, magnesium, potassium, zinc, iron and other metals in trace amounts) may be used. As an alternative culture medium a Czapek-Dox, optionally enriched with one or more ingredients, is used. A temperature between 0° and 45° C. and a pH between 3.5 and 8 is maintained during the growth of the microorganisms.

Preferably the microorganisms are grown at a temperature between 20° and 37° C. and at a pH between 4 and 7.

The aerobic conditions required during the growth of the microorganisms can be provided according to any of the well-established procedures, provided that the supply of oxygen is sufficient to meet the metabolic requirement of the microorganisms. This is most conveniently achieved by supplying gaseous oxygen, preferably in the form of air. During the stereospecific inversion the microorganisms might be in a growing stage using an abovementioned ordinary culture medium.

Preferably during the stereospecific inversion, the microorganisms can be held in a substantially non-growing stage using a minimal culture medium. As minimal culture medium, an ordinary culture medium may be used containing an assimilable carbon source when required (for example glucose, lactate, sucrose, etc.), a nitrogen source when required (for example ammonium sulphate, ammonium nitrate, ammonium chloride, etc.), with an agent for an organic nutrient source when required (for example yeast extract, salt extract, peptone, meat extract, etc.) and an inorganic nutrient source when required (for example phosphate, magnesium, potassium, zinc, iron and other metals in trace amounts). The microorganisms can be kept in the non-growing stage for example under exclusion of the assimilable carbon source or under exclusion of the nitrogen source. A temperature between 0° and 45 C and a pH between 3.5 and 8 is maintained during this stage. Preferably the microorganisms are kept at a temperature between 20° and 37° C. and a pH between 4 and 7. The aerobic conditions required during this stage can be provided according to the abovementioned procedures, provided that the supply of oxygen is sufficient to meet the metabolic requirement of the microorganisms but also to convert the R enantiomer into the corresponding S enantiomer.

The S-enantiomer produced by the microorganisms as mentioned above, can be recovered and purified according to any of the procedures known per se for such products.

It has been found that the microorganisms employed in the process according to the invention are capable of converting the R-enantiomer to the S-enantiomer, but not the S-enantiomer to the R-enantiomer. Accordingly, the process according to the invention may be used to prepare the S-enantiomer substantially free of the R-enantiomer, without the need for subsequent resolution. This is both surprising and advantageous.

It has also been found that the R-enantiomers of aryl propionic acids closely related in structure to 2-(6-methoxy-2-naphthyl)propionic, in particular 2-(4-isobutylphenyl)-propionic acid (ibuprofen) and 2-(2-fluoro-4-biphenyl)propanoic acid (flurbiprofen), are not covered into the corresponding S-enantiomers by the method of the process according to the invention. Accordingly, the fact that the R-enantiomer of 2-(6-methoxy-2-naphthyl)propionic acid may be converted into the S-enantiomer is particularly surprising.

The invention is illustrated in the following examples. The media used were as follows:

| Czepek Dox Quantities given g/l | |
| --- | --- |
| sodium nitrate | 3.00 |
| potassium chloride | 0.50 |
| magnesium glycerophosphate | 0.50 |
| ferrous sulphate | 0.01 |
| potassium sulphate | 0.35 |
| sucrose | 30 |
| Additions: 0.1% (w/v) malt extract and 0.1% (w/v) yeast extract. pH adjusted to 5.5. | |
| Phosphate Medium (PSX) Quantities in g/l | |
| Potassium dihydrogen phosphate | 8.92 |
| disodium hydrogen phosphate | 2.84 |
| diammonium hydrogen phosphate | 1.0 |
| ammonium sulphate | 0.2 |
| potassium chloride | 0.2 |
| trisodium citrate | 0.294 |
| calcium sulphate .2H$_2$O | 0.005 |
| magnesium sulphate .7H$_2$O | 0.2 |
| PS 2 T/E | 10.0 ml/l |
| PS2 T/E | |
| (NH$_4$)$_2$ SO$_4$.FeSO$_4$.6H$_2$O | 0.25 g |
| ZnSO$_4$.7H$_2$O | 0.05 g |
| MnCl$_2$.4H$_2$O | 0.03 g |
| CuSO$_4$.5H$_2$O | 0.015 g |
| CoCl$_2$.6H$_2$O | 0.015 g |
| H$_3$BO$_3$ | 0.005 g |
| Na$_2$MoO$_4$.H$_2$O | 0.0055 g |
| KI | 0.01 g |
| Dissolved in 1 litre distilled water | |
| Minimal Growth Medium Quantities in g/l | |
| ammonium nitrate | 1.2 |
| ammonium sulphate | 2.0 |
| potassium dihydrogen phosphate | 1.5 |
| disodium hydrogen phosphate | 1.5 |
| potassium sulphate | 0.5 |
| magnesium sulphate .7H$_2$O | 0.4 |

| -continued | |
| --- | --- |
| ferrous sulphate | 0.1 |
| calcium chloride .2H$_2$O | 0.066 |
| zinc sulphate .7H$_2$O | 0.0107 |
| manganese sulphate .4H$_2$O | 0.0066 |
| copper sulphate .5H$_2$O | 0.0031 |
| boric acid | 0.0004 |
| sodium molybdate .2H$_2$O | 0.0012 |
| cobalt chloride .6H$_2$O | 0.0007 |
| nitrilotriacetic acid trisodium salt | 0.2 |
| pH adjusted to 5.5. | |
| Minimal salts medium (PSIII) pH 7.0 | |
| KH$_2$PO$_4$ | 2.1 g/l |
| (NH$_4$)2HPO$_4$ | 1.0 g/l |
| (NH$_4$)$_2$HSO$_4$ | 0.9 g/l |
| KCl | 0.2 g/l |
| CaSO$_4$.2H$_2$O | 0.005 g/l |
| MgSO$_4$.7H$_2$O | 0.2 g/l |
| (NH$_2$)SO$_4$.FeSO$_4$.6H$_2$O | 2.5 mg/l |
| ZnSO$_4$.7H$_2$O | 0.5 mg/l |
| MnCl$_2$.4H$_2$O | 0.3 mg/l |
| CuSO$_4$.5H$_2$O | 0.15 mg/l |
| CoCl$_2$.6H$_2$O | 0.15 mg/l |
| H$_3$BO$_3$ | 0.05 mg/l |
| Na$_2$MoO$_4$.2H$_2$O | 0.055 mg/l |
| KI | 0.1 mg/l |
| pH adjusted to 6.8 | |

EXAMPLE 1

Conversion of R-2-(6-methoxy-2-naphthyl)propionic acid into S-2(6-methoxy-2-naphthyl)propionic acid using *Cordyceps militaris* CBS 267.85

*Cordyceps militaris* CBS 267.85 was kept on Czapek-Dox agar slants and inoculated for use into Czapek Dox medium and grown at 25° C. for 5 days in a 250 ml conical flask containing 50 ml medium with shaking and maintenance of aerobic conditions.

The mycelium was harvested and reincubated in 50 ml minimal growth medium as described above with maintenance of shaking and aerobic conditions. R-2-(6-methoxy-2-naphthyl)propionic acid (20 mg) was added to the culture which was incubated for a further 4 days at 25° C.

The culture was acidified to pH 2.0 with 5N hydrochloric acid and the mixture extracted with dichloromethane.

The quantities of acid recovered were determined by HPLC (Gilson isocratic system) under the following conditions:

| | |
| --- | --- |
| UV detection: | 254 nm |
| column: | Spherisorb S50DS2 (250 × 4.9 mm) |
| mobile phase: | 50 mM potassium dihydrogen phosphate adjusted to pH 3.7 with phosphoric acid, 35% (v/v) in methyl cyanide. |
| flow rate: | 1.5 ml/min |
| injection: | 5 μl |
| temperature: | ambient |
| retention time: | approx. 3.1 minutes |

Derivatisation and chiral HPLC analysis was carried out as follows:

Derivatisation to naphthalene methylamides: The dichloromethane extract (3 ml) was reacted with 200 μl bromomethyl pyridinium iodide (5% w/v in dimethyl formamide) and 200 μl 1-naphthalene methylamine solution (10% v/v in dichloromethane). The mixture was vortexed and heated at 60° C. for 10 minutes and then dried under nitrogen and extracted with isooctane/dichloromethane (2:1 v/v) (3 ml) and 0.5M sulphuric acid (2 ml).

| Chiral HPLC conditions: | |
| --- | --- |
| UV detection: | 280 nm |
| column: | Baker bond DNPG (250 × 4.9 mn) |
| mobile phase: | isooctane/methanol/chloroform (90:3:7 v/v) |
| flow rate: | 2 ml/min |
| injection: | 20 μl |
| temperature: | ambient |
| retention times: | S - enantiomer approx. 24 minutes |
| | R - enantiomer approx. 26 minutes |

Inversion of the R-enantiomer into the S-enantiomer was observed. All the acid recovered (7.8 mg; 39%) was in the S form.

A comparison experiment using S-enantiomer as the supply to the microorganism did not result in accumulation of the corresponding R-enantiomer.

EXAMPLE 2

Conversion of R/S-2-(6-methoxy-2-naphthyl)propionic acid into S-2(6-methoxy-2-naphthyl)propionic acid using *Cordyceps militaris* CBS 267.85

The procedure of Example 1 was repeated except that 20 mg of racemic 2-(6-methoxy-2-naphthyl)propionic acid was used as substrate. Incubation of the substrate with the cells was carried out for 24 hours followed by extraction and analysis as described in Example 1 to yield the acid product (11.6 mg; 58%). The percentage of S-enantiomer in the recovered acid was found to be 88%.

EXAMPLES 3 TO 6

Conversion of R-2-(6-methoxy-2-naphthyl)propionic acid into S-2-(6-methoxy-2-naphthyl)propionic acid The procedure of Example 1 was repeated using the microorganisms listed in Table 1 below to give the indicated percentage of S-enantiomer in the product. The microorganism *R. Rhodochrous* NCIB 12566 was grown at 30° C. in PSX medium as described above on heptane supplied as a vapour from a centre well. The remaining microorganisms were grown as described in Example 1. When using *B. bassiana* DSM 875, 50 mg of substrate was employed, whereas 20 mg substrate was employed in the remaining experiments.

Comparative experiments starting with the S-enantiomer did not result in accumulation of the corresponding R-enantiomer.

EXAMPLE 7

Preparation of S-2-(6-methoxy-2-naphthyl)propionic acid using *Exophiala Wilhansii* CBS 547.88

*Exophiala wilhansii* (CBS 547.88) was inoculated for use into a minimal salts medium (PSIII) supplemented with yeast extract (0.01 w/v%) and glycerol (0.5 w/v%) and grown at 30° C. for 48 hours in a 500 ml baffled flask containing 100 ml medium with shaking.

The culture was diluted 20-fold in fresh medium and grown at 30° C. for 24 hours. The cell mass was collected by centrifugation and resuspended in the same medium without glycerol. The cell concentration of the suspension was 10–15 mg cell dry mass per ml.

Two ml soyoil or 2 ml 7.5% Tween-80 (TM) or 2 ml medium containing 5 mg 2-(6-methoxy-2-naphthyl)-propanoic acid (R/S or R) was added to 10 ml suspensions. The mixtures were shaken in 125 ml baffled flasks at 30° C. for the time indicated.

The suspensions were acidified to pH 2.0 with 85% phosphoric acid and then extracted with dichloromethane.

The quantities of acid recovered were determined by HPLC, as described below. The enantiomeric ratio of the acid was determined by chiral HPLC, after derivatization, as described below. The results are given in Table 2 (R/S acid starting material) and Table 3 (R acid starting material).

Quantification of 2-(6-methoxy-2-naphthyl)propionic acid

Two ml of extract was concentrated by evaporation under nitrogen at 60° C. The residue was dissolved in 2 ml acetonitrile/water (2:1, v/v) and analyzed with HPLC using a Chrompack Polygosyl 60 D 10 CN column (250 mm, diameter 4.6 mm) eluted with acetonitrile/0.03 MNaH$_2$PO$_4$(36:64, v/v) pH 5.0. The acid was detected spectrophotometrically at 254 nm.

Determination of the enantiomeric purity of 2-(6-methoxy-2-naphthyl)propionic acid Eight to twelve ml of extract was concentrated by evaporation under nitrogen at 60° C. The dried residue was dissolved in 2 ml dichloromethane and allowed to react for 10 min. at 60° C. with 200 μl of a solution of 2-bromo-1-methyl-pyridiniumiodide in dimethylformamide (50 mg/ml) and 200 μl of a solution of 1-naphthalene methylamine in dichloromethane (100 mg/ml). The reaction mixture was dried under nitrogen at 60° C. The residue was dissolved in 2 ml isooctane/dichloromethane (2:1, v/v) and extracted after addition of 2 ml 1N HCl. The organic layer was dried and analyzed with HPLC using a Baker, aminopropyl covalent DNBPG column (250 nm, diameter 4.6 mm) and eluted with isooctane/chloroform/methanol (90:7:3, v/v/v). Compounds were detected spectrophotometrically at 280 nm.

COMPARATIVE EXAMPLE

Inversion of other 2-Arylpropionic Acids (a) 2-(4-Isobutylphenyl)propanoic acid (Ibuprofen)

The inversion of either enantiomer of Ibuprofen was tested using the following microorganisms grown as indicated in example 1. Substrates were used at 10 mg per 50 ml of culture. Product isolation, and characterisation was carried out as previously described using single enantiomers as reference compounds.

TABLE 4

| Microorganism | Enantiomer added | Enantiomeric ratio in product (S:R) | Recovery |
| --- | --- | --- | --- |
| C. resinae | S | 95:5 | 28 |
| CBS 177.62 | R | 4:96 | 33 |
| B. bassiana DSM 875 | R | 2:98 | 57 |
| C. militaris | S | 76:24 | — |
| CBS 267.85 | R | 6:94 | — |
| E. jeanselmei | S | 63:37 | 50 |
| CBS 258.86 | R | 3:97 | 47 |

TABLE 4-continued

| Microorganism | Enantiomer added | Enantiomeric ratio in product (S:R) | Recovery |
|---|---|---|---|
| E. Wilhansii CBS 547.88 | R | 4:96 | |

(b) 2-(2-Fluoro-4-biphenyl)propanoic acid (Flurbipiofen)

The first four organisms listed in Table 4 did not invert the R or the S enantiomer of Flurbiprofen. E. wilhansii CBS 547.88 did not invert the R enantiomer and gave 100% recovery.

TABLE 1

| Ex. | Strain | Incubation (days) | % S enantiomer | % Recovery |
|---|---|---|---|---|
| 3. | B. bassiana DSM 875, ATCC 13144 | 4 | 100 | 6 |
| 4. | C. resinae CBS 177.62 | 3 | 74 | 15 |
| 5. | E. jeanselmei CBS 258.86 | 4 | 54 | 5 |
| 6. | R. rhodochrous NCIB 12566 | 4 | 5 | 50 |

TABLE 2

Conversion of (R/S)-2-(6-methoxy-2-naphthyl)propionic acid into (S)-2-(6-methoxy-2-naphthyl)propionic acid using Exophiala wilhansii CBS 547.88

| detergent/oil present | incubation (hrs) | enantiomeric ratio (R/S) | recovery (%) |
|---|---|---|---|
| none | 24 | 32/68 | 74 |
| Tween-80 | 16 | 0/100 | 92 ± 14* |
| Soyoil | 16 | 0/100 | 43 |

*Experiment has been performed in triplicate. The results demonstrate that the use of a detergent in the process is particularly advantageous.

TABLE 3

Conversion of the (R)-enantiomer of 2-(6-methoxy-2-naphthyl)-propionic acid using Exophiala wilhansii CBS 547.88

| substrate* | incubation (hrs) | enantiomeric ratio (R/S) | recovery (%) |
|---|---|---|---|
| R-enantiomer | 8 | 61/39 | 100 |
| | 16 | 0/100 | 80 |

*Substrate was added as a solution in 7.5% Tween-80 (TM) as described above.

We claim:

1. A process for the preparation of S-2-(6-methoxy-2-naphthyl)propionic acid, which comprises supplying R-2-(6-methoxy-2-naphthyl)propionic acid, to a microorganism having a stereospecific inverting enzyme system, or an extract of the microorganism containing said enzyme system, capable of converting the R enantiomer to the corresponding S enantiomer.

2. A process as claimed in claim 1, in which the R acid is supplied to the microorganism.

3. A process as claimed in claim 2, in which the R acid is supplied to the microorganism in the form of a racemic mixture with the S enantiomer.

4. A process as claimed in any one of claims 1 to 3, in which the microorganism is a fungus of the genus Cordyceps, Beauveria, Cladosporium or Exophiala.

5. A process as claimed in claim 4, in which the microorganism belongs to the species Cordyceps militaris, Beauveria bassiana, Cladosporium resinae, or Exophiala jeanselmei.

6. A process according to claim 5 wherein the microorganism is Cordyceps militaris CBS 267.85, Beauveria bassiana DSM 875, ATCC 13144, Cladosporium resinae CBS 177.62 or Exophiala jeanselmei CBS 258.86, or a variant or mutant thereof.

7. A process according to any one of claims 1, 2 or 3 wherein the product of the stereospecific inversion is in the form of a free acid which is subsequently converted to a pharmaceutically acceptable salt or ester.

8. A process according to claim 1 wherein the acid product is subsequently converted to a pharmaceutically acceptable salt or ester.

* * * * *